US010977590B2

(12) United States Patent
Perry

(10) Patent No.: US 10,977,590 B2
(45) Date of Patent: Apr. 13, 2021

(54) COMPUTERIZED DATA PROCESSING SYSTEMS AND METHODS FOR GENERATING GRAPHICAL USER INTERFACES

(71) Applicant: TeleTracking Technologies, Inc., Pittsburgh, PA (US)

(72) Inventor: Thomas Perry, DuBois, PA (US)

(73) Assignee: TeleTracking Technologies, Inc., Pittsburgh, PA (US)

(*) Notice: Subject to any disclaimer, the term of this patent is extended or adjusted under 35 U.S.C. 154(b) by 0 days.

(21) Appl. No.: 16/672,661

(22) Filed: Nov. 4, 2019

(65) Prior Publication Data

US 2020/0065741 A1    Feb. 27, 2020

Related U.S. Application Data

(63) Continuation of application No. 15/428,250, filed on Feb. 9, 2017, now Pat. No. 10,467,566.
(Continued)

(51) Int. Cl.
*G06Q 10/06* (2012.01)
*G06F 16/29* (2019.01)
(Continued)

(52) U.S. Cl.
CPC ... *G06Q 10/063114* (2013.01); *G06F 3/0482* (2013.01); *G06F 3/04817* (2013.01);
(Continued)

(58) Field of Classification Search
CPC ............. G06Q 10/063114; G06F 16/29; G06F 16/2477; G06F 3/04817; G06F 3/0482; G16H 40/63; G16H 40/20
(Continued)

(56) References Cited

U.S. PATENT DOCUMENTS

2010/0121480 A1* 5/2010 Stelzer ................. B65G 1/1373
                                                              700/215
2010/0152544 A1* 6/2010 Weaver ................. G16H 15/00
                                                              600/300
(Continued)

OTHER PUBLICATIONS

"Indoor positioning system—Wikipedia", retrieved Jan. 26, 2016, URL: https://en.wikipedia.org/w/index.php?title=Indoor_positioning_system&oldid=701727006. XP055361196, 9 pages.

*Primary Examiner* — Bo Fan
(74) *Attorney, Agent, or Firm* — Ference & Associates LLC

(57) ABSTRACT

Computer-implemented systems and methods generate dynamic and interactive user interfaces. In one embodiment, a computerized system includes a user interface and at least one processor configured to receive data related to at least a first request of a department, receive data related to positioning of a plurality of employees of the department, and data indicative of equipment in the possession of the plurality of employees, generate an assignment for at least one employee based on the received data, provide for display at the at least one user interface, an interactive graphical user interface indicative of the assignment to the at least one employee, the graphical user interface including elements for indicating a status of the assignment. The at least one processor monitors whether the assignment has been accepted, and determines whether the assignment has been completed, based in part on interaction with the graphical user interface.

20 Claims, 10 Drawing Sheets

Related U.S. Application Data

(60) Provisional application No. 62/292,935, filed on Feb. 9, 2016.

(51) Int. Cl.
| | |
|---|---|
| *G06F 16/2458* | (2019.01) |
| *G16H 40/63* | (2018.01) |
| *G16H 40/20* | (2018.01) |
| *G06F 3/0481* | (2013.01) |
| *G06F 3/0482* | (2013.01) |

(52) U.S. Cl.
CPC .......... *G06F 16/2477* (2019.01); *G06F 16/29* (2019.01); *G16H 40/20* (2018.01); *G16H 40/63* (2018.01)

(58) Field of Classification Search
USPC ........................................ 705/2, 3, 216, 229
See application file for complete search history.

(56) References Cited

U.S. PATENT DOCUMENTS

| | | | |
|---|---|---|---|
| 2010/0217618 A1* | 8/2010 | Piccirillo | G06Q 50/22 |
| | | | 705/2 |
| 2013/0246090 A1* | 9/2013 | Hoffman | G06Q 10/10 |
| | | | 705/2 |
| 2014/0136223 A1* | 5/2014 | Phillips | G16H 10/60 |
| | | | 705/2 |
| 2015/0100333 A1 | 4/2015 | Fitzgerald et al. | |
| 2015/0186829 A1* | 7/2015 | Khan | G06Q 10/103 |
| | | | 705/7.15 |
| 2015/0269825 A1 | 9/2015 | Tran | |

\* cited by examiner

FIG. 7

COMPUTERIZED DATA PROCESSING SYSTEMS AND METHODS FOR GENERATING GRAPHICAL USER INTERFACES

PRIORITY CLAIM

This application is a continuation of U.S. application Ser. No. 15/428,250, filed Feb. 9, 2017, which claims priority from to U.S. Provisional Application No. 62/292,935, filed Feb. 9, 2016. The aforementioned applications are which is hereby incorporated by reference in its entirety their entireties in the present application.

TECHNICAL FIELD

The subject matter described herein generally relates to electronic data processing systems that generate and provide graphical user interfaces (GUIs) in a centralized communication system, using real time data collected from a plurality of networked sources. More particularly, disclosed embodiments are directed to centralized communication systems for generating automated electronic messages in a facility based on detected events. The data processing system may automate one or more processes in response to the detected events and automatically distribute electronic messages to a plurality of networked devices.

BACKGROUND

Modern hospitals treat and discharge hundreds of patients every day, requiring frequent transportation of patients, equipment, and other items between points in the hospital. Every minute of time lost because of insufficient workflow significantly impacts the hospital's performance and the patient's health.

Traditional hospital management is time consuming, prone to error, and significantly underutilizes the capabilities of each department. Different hospital units and departments often lack sufficient communication systems. Traditional techniques involve telephone-based manual reporting of an event and/or manual requests for transport, usually through phone calls between individuals in the facility. For example, in traditional systems, a requester may place a telephone call to a phone number, and request a transport service or provide information about a transport status. The requester may interact with a computerized interactive voice response (IVR) system, which then processes the received information for review by a dispatcher to identify and direct a transporter in response to the request or event, or manually queue the request to be assigned automatically. Current systems rely solely on information received during a manual telephone call, which can be sporadic and/or untimely, and can include incorrect information. Moreover, because traditional systems rely on telephone calls and IVR-based processing, traditional systems often experience very high call volumes which strain communication networks in the facility. In many instances, unnecessary and redundant calls also increase network strain, and traditional systems usually result in overloaded telephone lines and missed requests, thereby degrading the quality and speed of transport of patients and equipment.

In view of the technical deficiencies of current systems discussed above, there is a need for improved systems and methods centralized real-time event detection and communication.

SUMMARY

Disclosed embodiments relate to systems and methods for centralized communication and generating graphical user interfaces based on real-time data for managing transportation of patients and/or items throughout a medical facility such as a hospital.

Consistent with the present embodiments, a computerized system is disclosed. The computerized system may include: at least one user interface; at least one processor; and a storage medium comprising instructions that, when executed by the at least one processor, generates a graphical user interface at the at least one user interface, by: receiving, at the at least one processor, a first set of data related to at least a first request of a department; receiving, with the at least one processor, a second set of data related to positioning of a plurality of employees of the department and equipment in the possession of the plurality of employees; generating, with the at least one processor, an assignment for at least one employee based on the first set of data and the second set of data; displaying, at the at least one user interface, the graphical user interface indicative of the assignment to the at least one employee; monitoring, with the at least one processor, whether the assignment has been accepted; and determining, with the at least one processor, whether the assignment has been completed.

Consistent with the present embodiments, a computerized method for generating a graphical user interface is disclosed. The computerized method may include: receiving, at the at least one processor, a first set of data related to at least a first request of a department; receiving, with the at least one processor, a second set of data related to positioning of a plurality of employees of the department and equipment in the possession of the plurality of employees; generating, with the at least one processor, an assignment for at least one employee based on the first set of data and the second set of data; displaying, at the at least one user interface, the graphical user interface indicative of the assignment to the at least one employee; monitoring, with the at least one processor, whether the assignment has been accepted; and determining, with the at least one processor, whether the assignment has been completed.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIG. 7 is an illustration of an example of a user interface, consistent with embodiments of the present disclosure.

DETAILED DESCRIPTION OF EXEMPLARY EMBODIMENTS

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
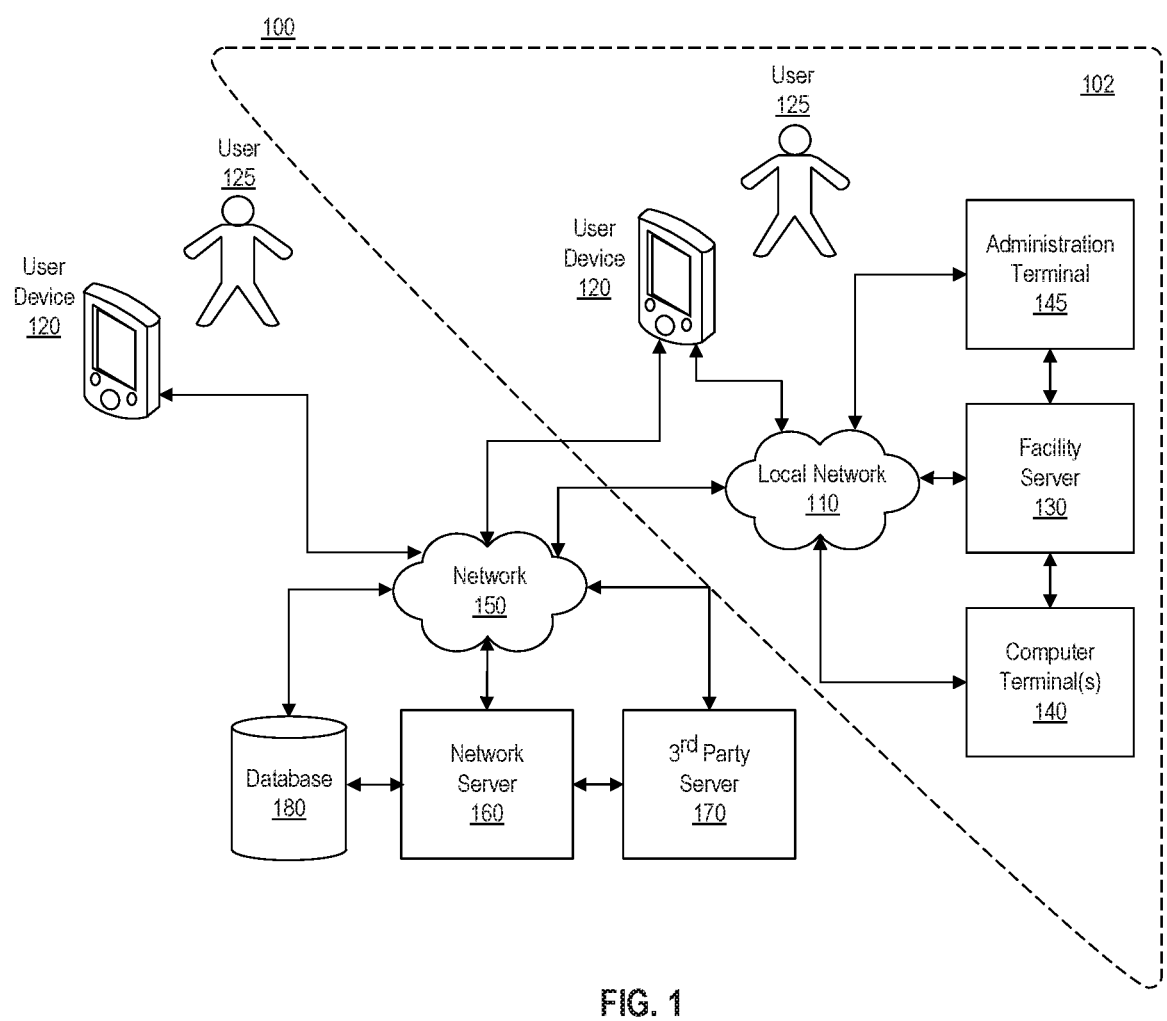
FIG. 1 depicts an example of a system environment for managing transport within a hospital, consistent with embodiments of the present disclosure.

FIG. 1 shows a diagram of a system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, a network server 160, a third party server 170, and a database 180. The components of system 100 may communicate directly, through a network 150, through a local network 110, or through a combination of communications methods. In some embodiments, local network 110, facility server 130, computer terminal 140, administration terminal 145, and user device 120 may be physically disposed within a facility such as a hospital or office building (e.g. a facility system 102) while network 150, network server 160, third party server 170, and database 180 may be external to the facility. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a bed, room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person. The wireless receivers may be configured to detect objects and receive information through radiofrequency, infrared, radiofrequency-infrared hybrid, optical, ultrasound, Bluetooth™, and/or barcode.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message received from a computer terminal 140 may automatically associate the message with the room in which computer terminal 140 is installed.

Administrator terminal 145 may include a computer system or a device associated with a user 125 that manages or oversees a portion of facility system 102. For example, administrator terminal 145 may comprise a computer system located at a head nurse station, a transporter dispatch station, or any other department manager's office or station.

User 125 may be one or more individuals associated with the patient or one or more items to be transported. Users 125 may operate computer terminal 140, user device 120, and/or another computer (not shown) to interact with system 100. Users 125 may be individuals located within and/or outside of the facility system 102, for example, transporters responsible for transporting patients and/or items. For example, users 125 may include physicians and nurses within the facility responsible for transporting the patients to different units. Users 125 may also include one or more individuals who are responsible for assignments, such as transporting patients and/or items throughout a hospital (e.g., facility 102). For example, users 125 may include doctors, nurses, porters, escorts, and/or volunteers. Users 125 may further include individuals outside of facility system 102, such as people with personal relationships with the patients (e.g. family members) and referring individuals (e.g. outside physicians and medics).

System 100 may be customizable and provide individualized access for each user 125. For example, in some embodiments, only certain users 125, such as physicians and nurses, may be allowed to generate transport requests. In some embodiments, one or more users 125, such as the patient's primary physician, may be required to authorize all requests. Users 125 solely responsible for specific tasks, such as a transport assignment, may have access limited to perform their responsibilities. It is also contemplated that some users 125, such as family members, may have read-only access.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that messages and/or task assignments directed toward user 125 are sent to user device 120. In some embodiments, user device 120 may communicate with facility server 130 and/or network server 160 via direct wireless communication links (not shown), or via a combination of one or more of local network 110 and/or network 150.

Facility server 130 may be operated by a facility such as a hospital. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™ Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service™, Azure Mobile Services™, or Google Cloud Messaging™. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
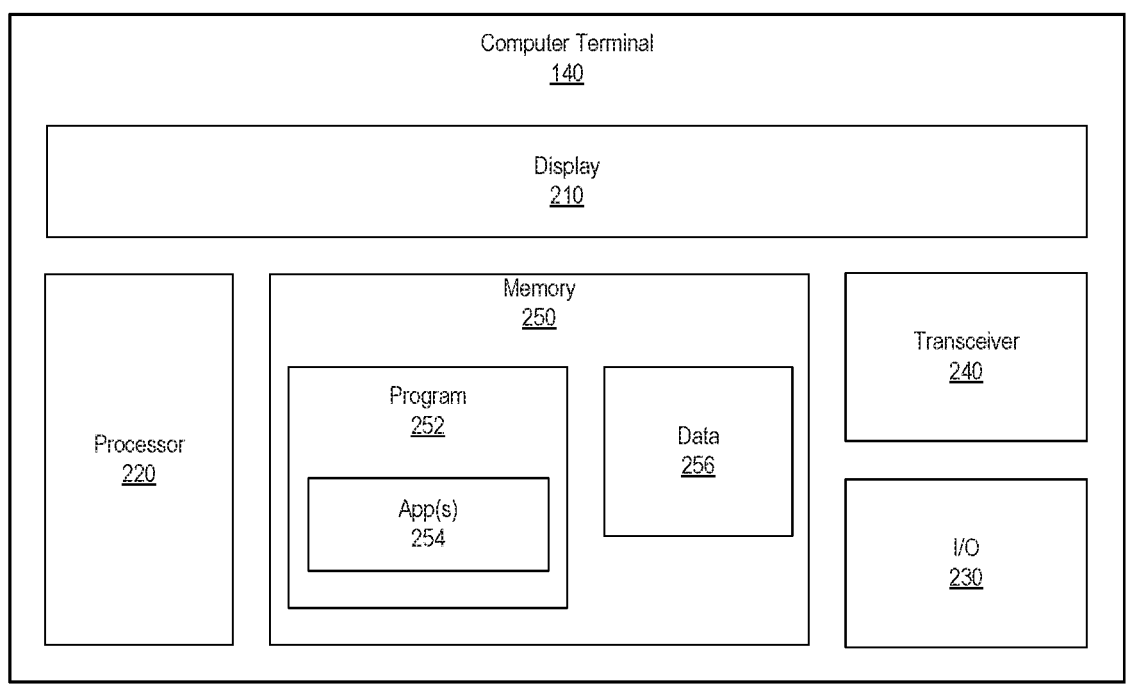
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from one or more users 125. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, hospital information, patient information, user information, task information, and display settings and preferences. For example, data 256 may include information related to patients and items to be transported, data 256 may also include information related to staff scheduling. In some embodiments, data 256 may further include one or more rules for analyzing and generating a task, such as a transportation assignment.

Program(s) 252 may include operating systems (not shown) that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™ or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a transportation management app, which when executed causes computer terminal 140 to perform processes related to managing, analyzing, prioritizing, and scheduling transportation assignments. For example, app(s) 254 may configure computer terminal 140 to perform operations including, for example, one or more of receiving transportation requests, receiving data from a variety of other sources, analyzing and generating a transportation assignment, monitoring the transportation assignment, and generating GUIs for users 125 that monitor and/or perform the transportation assignments.

Figure 3:
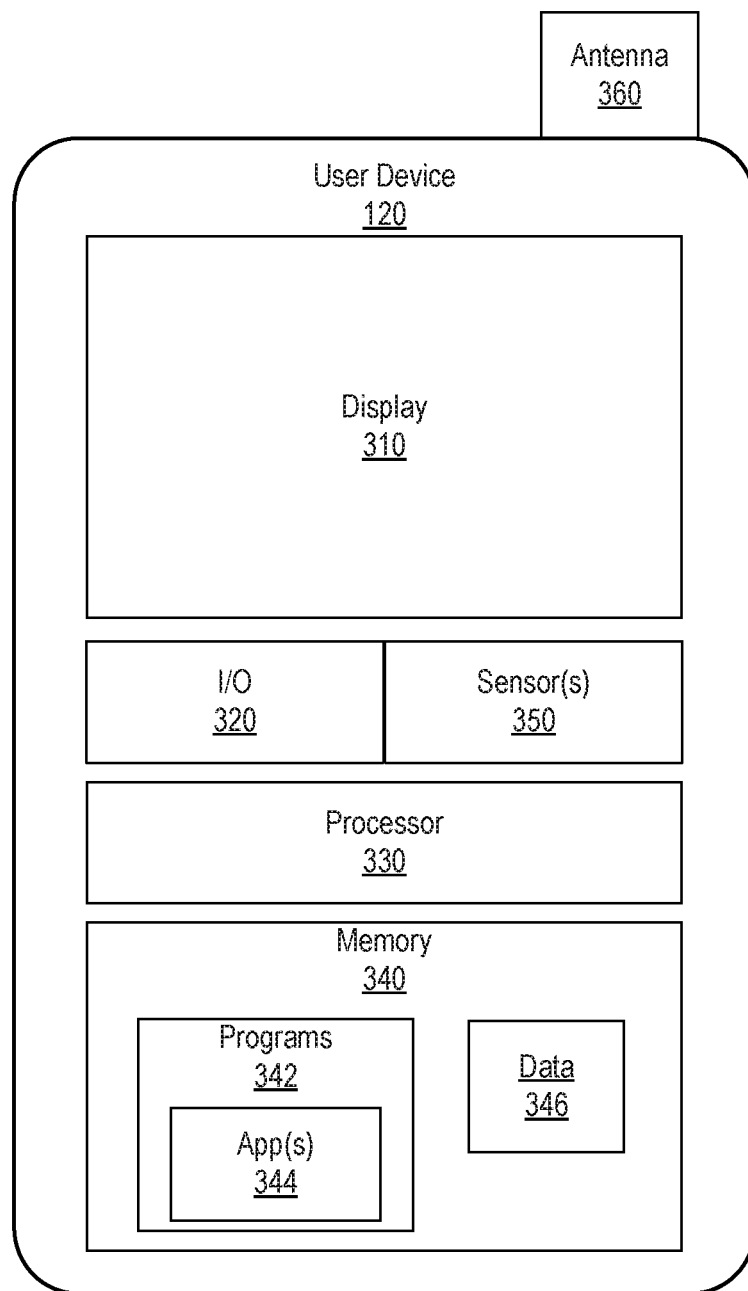
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between user device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
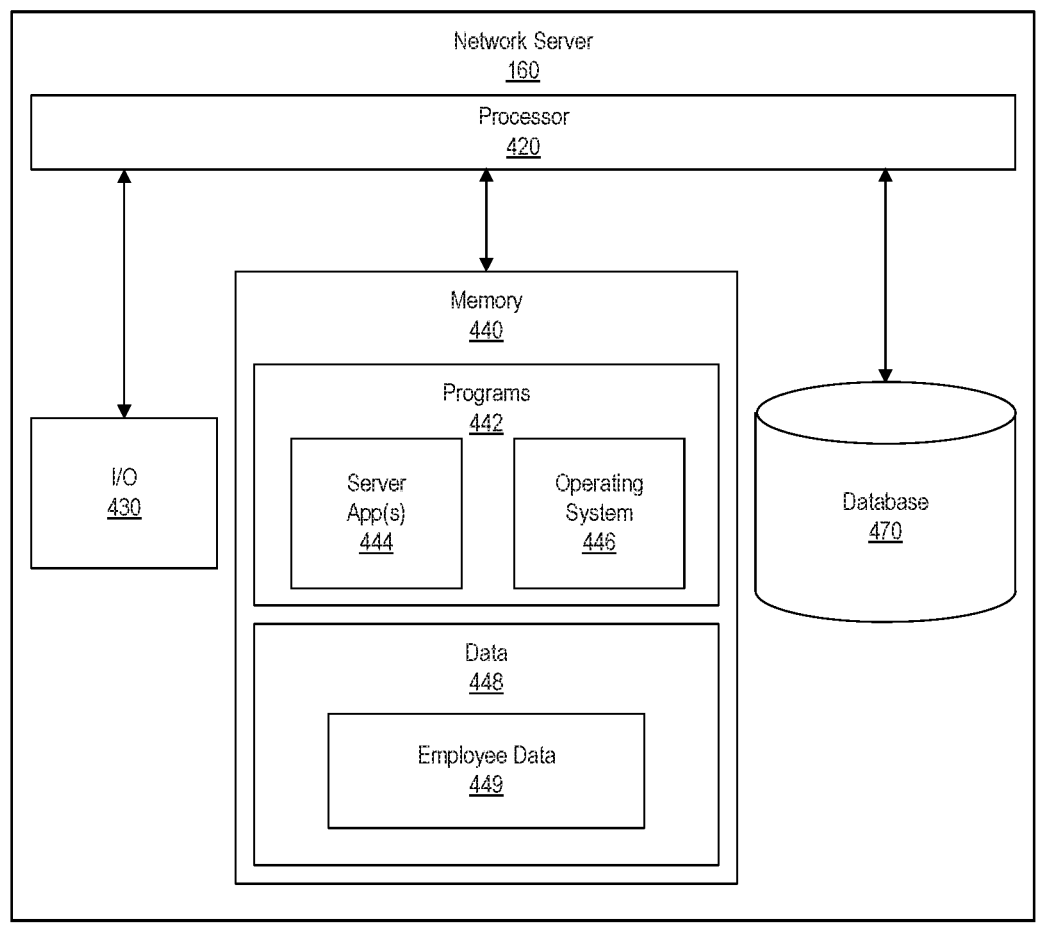
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as transporting patients between facilities. Additionally, network server 160 may collect data from multiple units to evaluate performance times in different units, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448, and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more users 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Additionally or alternatively, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 442 stored in memory 440 and executed by processor(s) 420 may include one or more server app(s) 452 and operating system 454. Server app(s) 452 may incorporate one or more apps to perform operations including, for example, one or more of receiving transportation requests, receiving data from a variety of other sources, analyzing and generating a transportation assignment, monitoring the transportation assignment, and generating GUIs for users 125 responsible for assigning transportation requests and transporters. In some embodiments, programs 442 may also include instructions that may be executed by processor 420 to perform a real time locating system (RTLS) through one or more wireless receivers of facility system 102. Processor 420 may utilize data from a RTLS to determine, either predictively or on demand, the exact proximity (such as a distance or travelling time) of employees (e.g., users 125) from patients, items to be moved, and/or equipment that facilitates the transportation. For example, processor 420 may be configured to utilize a RTLS to identify and track tagged objects and people, and conditions of thereof. For example, objects and/or people may be equipped with a badge/tag that emits an RFID signal that may be detected by the wireless receivers of facility system 102. In some embodiments, processor 420 may detect the locations of patients and determine their statuses. For instance, processor 420 may determine that the patient is still occupying a bed when patient is located in or around the bed. Processor 420 may also determine if the patient has been discharged, for example, by determining that the patient is in a lobby of facility system 102 for a certain period of time. Processor 420 may also track employees (e.g., users 125) by tracking GPS data of user devices 120. For example, processor 420 may determine the location of employees, based on a floor, a department, and/or a room. Based on the location and a direction of movement, processor 420 may determine whether an employee is currently on a transport assignment, moving to a pick-up for a transport assignment, moving away from a drop-off for a transport assignment, and/or transitioning between transport assignments. In some embodiments, the RTLS data may be processed to determine derived data. For example, the RTLS data may be processed to determine derived data, such as speed, acceleration, efficiency, and/or frequent locations. Processor 420 may store the RTLS data and derived data, for example, in database 470 to be later accessed for methods of this disclosure.

In some embodiments, memory 440 may store data 448 including data associated with hospitals, units, patients, employees, tasks, assets, assignment algorithms, and any other data related to the disclosed embodiments. For example, data 448 may include one or more entries including information pertaining to employees (e.g., users 125) including identification, scheduled work assignments, personal traits, capabilities, and preferences. Data 448 may also include information pertaining to patients, such as identification, scheduled medical events, medical history, and other personal traits. Data 448 may further include information pertaining to objects, such as size, weight, previous locations, and most common locations. In some embodiments, data 448 may be stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
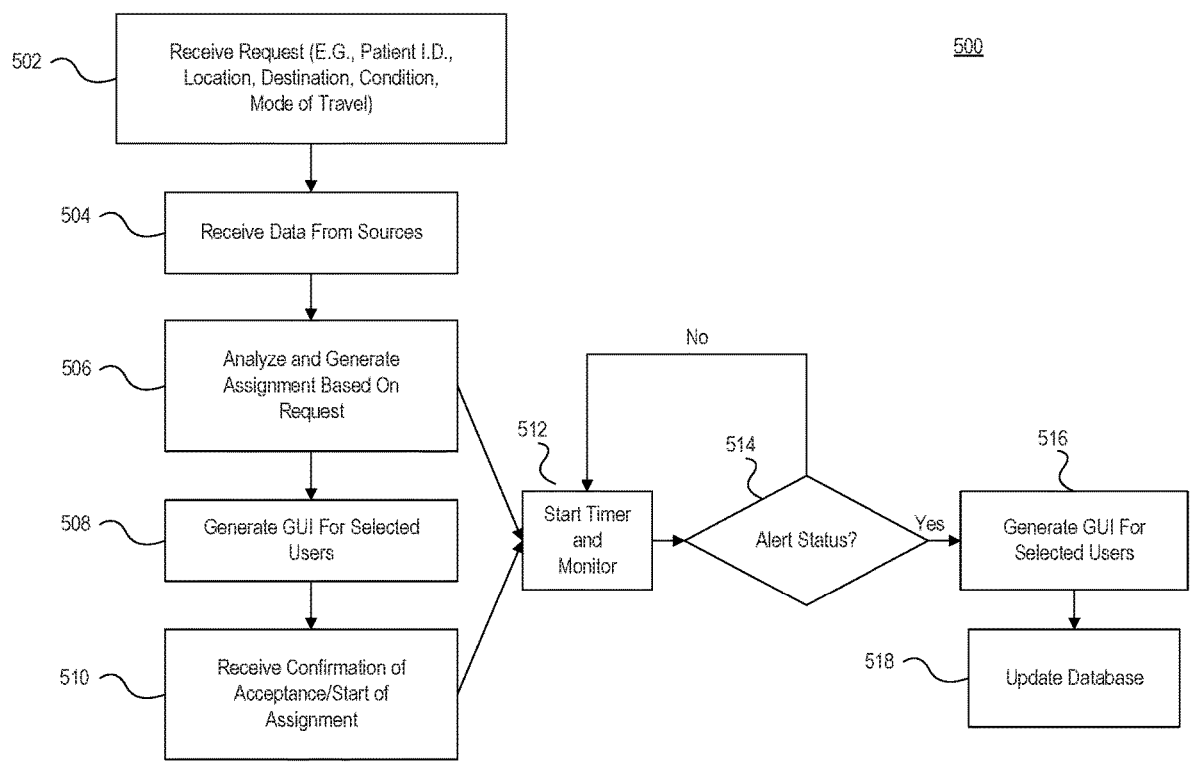
FIG. 5 is a flowchart of an example of a transport tracking process, consistent with embodiments of the present disclosure.

FIG. 5 shows a flowchart of an exemplary transport tracking process 500. Process 500 may expedite the transportation and monitoring of patients and/or items throughout a system (e.g., facility system 102). Process 500 is described herein as performed primarily by network server 160, however in some embodiments, facility server 130, computer terminal 140, administrator terminal 145, user device 120, and/or third party server 170 may perform one or more steps of process 500.

Process 500 may be performed with other applications and/or components, and receive data from a number of different sources. In some embodiments, process 500 may be used in conjunction with one or more app(s) performed by at least one of network server 160, facility server 130, computer terminal 140, administrator terminal 145, user device 120, and/or third party server 170. For example, network server 160 may be configured to perform process 500 in conjunction with apps, such as employee time entry, real-time patient placement, bed tracking, and/or workflow management. Accordingly, the data received in process 500 may be generated by the apps.

Process 500 may begin in step 502 when network server 160 receives and processes data related to a requested task. In some embodiments, the data may relate to the transportation of one or more patient(s) and/or item(s) in a hospital (e.g., facility system 102). For example, the items may include wheelchairs, beds, IV poles, laboratory samples, and/or tissue transplants. In some embodiments, the requests may include patients/items transported between rooms, floors, units, and/or hospitals. The request may be generated by data from one or more of user device 120, computer terminal 140, administration terminal 145, an intercom, and/or a station phone of facility system 102.

In some embodiments, the received data of step 502 may include detailed information of a patient, such as a name, an identifying number, an age, date of birth, a condition, current location, visit number, medical record number (MRN), and/or any additional information pertinent to the patient. For example, the received data may indicate whether the patient has any transmittable diseases (e.g., MRSA) that require additional care. For items, the received data may include the type of the item, the size of the item, and the weight of the item. The received data may also include a current location of and/or one or more destinations of the transportation. The received data may further include a desired mode of travel or any requirements of a user 125 to perform the transportation. For example, the received data may indicate whether the patient requires a wheel chair or bed for the requested transport. The received data may also include whether the patient/item needs automobile transportation (e.g., an ambulance), for example, from facility system 102 to another facility system 102. The received data may include the priority of the request, for example, "low", "medium", or "high". The received data may also include information of the requester, such as name, contact information, and department.

Figure 6:
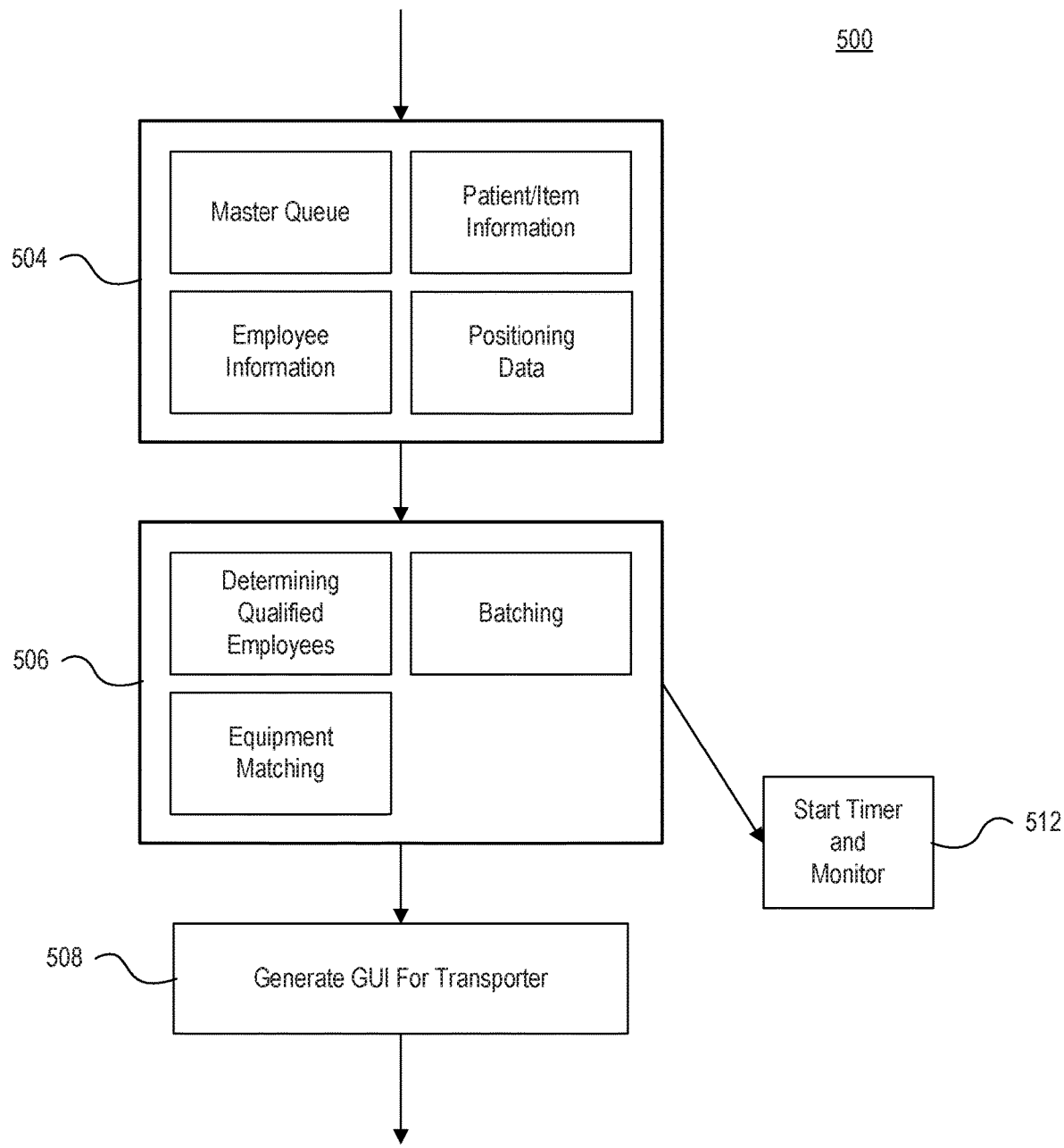
FIG. 6 is a flowchart of an example of steps of the exemplary transport tracking process of FIG. 5, consistent with embodiments of the present disclosure.

In step 504, network server 160 may receive additional data related to the patient/item of step 502 and/or one or more user(s) 125 that may be assigned to the requested task, as further depicted in FIG. 6. The additional data may be received from a number of different sources over a network, such as local network 110 and/or network 150. For example, the additional data may be received from app(s) performed by at least one of network server 160, facility server 130, computer terminal 140, administration terminal 145, user device 120, and/or third party server 170.

In some embodiments, network server 160 may receive a master queue, including related and/or unrelated assignments from database 180, or from any other memory associated with components of system 100. For example, the master queue may include previous and current transportation requests. The master queue may also include the previous transportation assignments. The master queue may further include a priority of each of the current requests. For example, each of the current requests may include a real-time numerical priority based on, for example, a destination, a status, a wait time, and/or other conditions. The priority may be continuously monitored and updated based on a change in conditions. In some embodiments, the priority may be based on a numerical scale (e.g., on a range of 1-10) indicating the relative need for the request. In some embodiments, the priority may be based on a location and/or destination of the transportation. For example, a first patient requested to be transported to X-ray may have a higher priority (e.g., an 8 on the scale) than a second patient requested to be discharged (e.g., a 6 on the scale). Accordingly, network server 160 may assign a user 125 to the transportation of the first patient prior to the second patient. In some embodiments, the priority may be based on a personal trait (e.g., age) and/or a medical history of the patient. In some embodiments, the priority may increase or decrease, for example, based on a wait-time of the patient or a pendency of the task being longer than a predetermined period of time. For example, the priority may increase every 5 minutes of wait-time, such that a patient that has been waiting for a longer period of time may have a higher priority. In some embodiments, the priority may decrease based on the pendency of other requests with higher priority. For example, the priority of each patient may be relative based on the number of patients that are requested to be transported. In some embodiments, the priority may be manually changed by an authorized user with appropriate rights, such as by an authorized user through user device 120 and/or administration terminal 145.

In some embodiment, network server 160 may receive additional patient/item information from database 180, or from any other memory associated with components of system 100. For example, the data may include any relevant information not received in step 502. The data may also include the status of one or more patients, including an indication of any medication or scheduled surgery. For instance, the data may indicate the patient recently was in surgery and currently under an anesthetic. The data may also indicate the size and shape of items and any special considerations based on the inputted type of item. For example, network server 160 may access the size and shape of the item according to look-up tables stored in one or more of database 180, memory 250, memory 340, and database 470. Network server 160 may also access scheduled information for the item to determine, for example, whether the item has recently been in contact with a patient having a transmittable disease (e.g., MRSA).

In some embodiments, network server 160 may receive employee (e.g., user 125) information from database 180, or from any other memory associated with components of system 100. In some embodiments, employee information may include one or more attributes associated with users 125 of the facility. For example, employee information may include a job title, certifications, qualifications, skill sets, dates and times scheduled to work, expected location of work, expected current location, detected current location, tasks currently assigned to user 125, a status of the assigned tasks, and performance data related to previous tasks. The data may also include information on whether user 125 is expected to be currently or recently in possession of any items, such as a wheel chair.

In some embodiments, network server 160 may receive positioning data from database 180, or from any other memory associated with components of system 100. For example, in some embodiments, the positioning data may be based on scheduling data indicative of one or more scheduled locations of a patient, item, or employee (e.g., user 125). The positioning data may also include RTLS data indicative of a detected real-time location of a patient, item, or employee. The positioning data may further include inputted data, such as previously determined locations of the patient, item, or employee. For example, that data may include one or more locations that the patient, item, or employee has been checked in. The current location may then be estimated based on scheduling data. In some embodiments, network server 160 may also generate positioning data in the form of behavioral data for the patient, item, or employee based on the received positioning data. For example, network server 160 may generate predictive models in an attempt to determine where the patient, item, or employee is located at different times of the day. Network server 160 may also update the predictive models based on additional received data.

In step 506, network server 160 may analyze and generate an assignment based on data from steps 502 and 504. In some embodiments, network server 160 may perform one or more processes to assign a task to an employee as further depicted in FIG. 6. The processes may be based on additional data accessed, for example, from look-up tables stored in one or more of database 180, memory 250, memory 340, and database 470.

In some embodiments, network server 160 may process data of the requested task of step 502 to determine one or more qualified employees for the request. For instance, network server 160 may access look-up tables to determine the required a job title, certifications, skill sets, skills required to complete the requested task. Network server 160 may also access employee information of step 504 and determine one or more employees suitable for the requested task. In some embodiments, network server 160 may generate a ranking of employees based on the qualifications for the job.

In some embodiments, network server 160 may batch items based on a related characteristic. For example, network server 160 may batch a plurality of items based on proximity of a current location and/or a destination. Network server 160 may also batch the items based on type. In some embodiments, network server 160 may identify one or more items having similar characteristics, and generate one or more transport tasks having multiple items of similar characteristics. Common characteristics may include, for example, a common origin or destination location, properties of the items that allow multiple similar items to travel together, close times of entry requests, and similar request priorities. In some embodiments, the similarity between item characteristics may be determined by determining whether the characteristics are within a predetermined amount of difference.

As an example of batch processing, network server 160 may group a plurality of tissue samples in a single transportation request based on the tissue samples being currently located in a common room or area. A single transporter may then deliver the tissue samples from common room/area to a plurality of locations. Network server 160 may also group a plurality of tissue samples to a transporter based on a common destination. For example, network server 160 may generate an assignment to the transporter to pick up tissue samples from different locations and deliver to a commoner room/area. Network server 160 may batch items on a temporally based on a current location and/or destination. For example, network server 160 may generate a second task for an employee based on a destination of a previously assigned first task ensuring a seamless transition from the first task to the second task. Network server 160 may also batch items based on other aspects of the master queue. For instance, if an expected wait time for an item is higher than a predetermined threshold, network server 160 may increase a range or number of items to be batched. For example, the predetermined threshold may be based on an urgency of the item. Perishable times, such as human tissue, may have a reduced predetermined threshold compared to non-perishable items, such as a wheel chair. Items may also be batched based on priority associated with the items. Batching items may increase efficiency and reduce unnecessary duplication of transportation tasks.

In some embodiments, network server 160 may also process the data to perform equipment matching. For example, in some embodiments, network server 160 may match an employee (e.g., user 125) who has equipment in hand, with a job that requires that equipment. For instance, network server 160 may determine that the employee recently completed a job where they used a wheelchair, such as returning a patient to their bed, and the employee now has an empty wheelchair. Network server 160 may determine that the employee has completed the job by, for example, receiving an indication of the completed job through user device 120, or by determining that the employee is located at the completed job destination location. Network server 160 may generate a new assignment in light of this information. For example, network server 160 may assign a high priority factor for the employee for jobs where a wheelchair is needed. In some embodiments, network server 160 may also access RTLS data to determine the locations of one or more wheelchairs relative to the employees (e.g., users 125). Network server 160 may then compare the location of the one or more wheelchairs to current or previously known locations of employees to determine relative distances. In some embodiments, network server 160 may determine whether the employee is in possession of the item based on a relative distance being less than a predetermined distance. Network server 160 may assign the requested tasks based on the equipment matching.

In some embodiments, step 506 may be performed at the desired time of execution and/or when the user(s) 125 is considered available. For example, step 506 may be performed to assign a single task to the employee at the time of execution. Assigning the tasks in real-time would enhance efficiency by ensuring that user(s) 125 is at the desired position at the desired time of execution. Network server 160 may also provide a more accurate assignment for user(s) 125 based on the current availability and position.

In step 508, network server 160 may generate a GUI for one or more selected user(s) 125. The selected user(s) 125 may include one or more user(s) 125 that are responsible for the task (e.g., transporting a patient and/or object). The selected user(s) 125 may be notified in a number of different manners, including a call, a text message, a push notification, a message within an app, and/or an email. Network server 160 may transmit the notification to user(s) 125 through one or more of user device 120, computer terminal 140, an intercom, and/or a station phone of facility system 102. In some embodiments, network server 160 may generate or update a GUI notifying user(s) 125 of the task. Network server 160 may send updates and reminders to the user(s) by generating or updated the GUI. Network server 160 may also recalculate or update the determination of selected user(s) 125 based on events, such as lack of acceptance from previously selected user(s) 125.

In step 510, network server 160 may receive confirmation of acceptance and/or start of the assignment. In some embodiments, network server 160 may automatically determine that user 125 has acknowledged the task if user device 120 associated with a user 125 indicates that the user 125 has accessed or viewed the notification for the task. In some embodiments, network server 160 may determine acknowledgement and acceptance based on an input received from user 125 via user device 120. In some embodiments, network server 160 may determine that acknowledgement acceptance based on one or more RTLS sensor devices. For example, network server 160 may determine user 125 accepted a task based on user 125 being located proximate the task. If no indication of acceptance is received after a predetermined amount of time (e.g., about 5 minutes), network server 160 may send a reminder notification to the selected user(s) 125 to ensure receipt. In some embodiments, if there is no acceptance from selected users 125, network server 160 may alter the determination of the selected user(s) 125 and send notifications to additional user(s) 125 in step 508 to increase chances that the task is completed.

In step 512, network server 160 may start a timer and monitor an alert status of the assignment. For example, network server 160 may monitor the situation to determine whether the task is completed. In some embodiments, the monitoring of the completion may be based on whether user 125 indicates that the task is completed. In some embodiments, the monitoring of the completion may be based on RTLS data, for example, indicating that the transported patient and/or item reaches the destination. Network server 160 may also generate an alert status based on the assignment pending for a time period longer than a predetermined time period. For example, network server 160 may determine whether the assignment has not been accepted or whether the assignment was accepted and not executed. In step 514, network server 160 may determine the presence of an alert status.

In step 516, network server 160 may generate a GUI for one or more selected user(s) 125. For instance, network server 160 may generate the indication by generating or updating a GUI including the status. The indication may be transmitted to one or more of user device 120, computer terminal 140, and/or third party server 170, similar to step 710. Selected users 125 may include requestor of step 502, selected users of steps 506-508, supervisors, and any other interested users 125.

In step 518, network server 160 may update a database. In some embodiments, network server 160 may record the identity of user 125 that received the notifications in step 706 and/or completed the task in steps 708 and/or 712. Network server 160 may also record the type of task, date, time, duration of task, and/or any other details of the performance of the task. In some embodiments, the network server 160 may update the database pursuant to each step 502-516. The data may be stored in one or more of one or more of database 180, memory 250, memory 340, and database 470.

Figure 7:
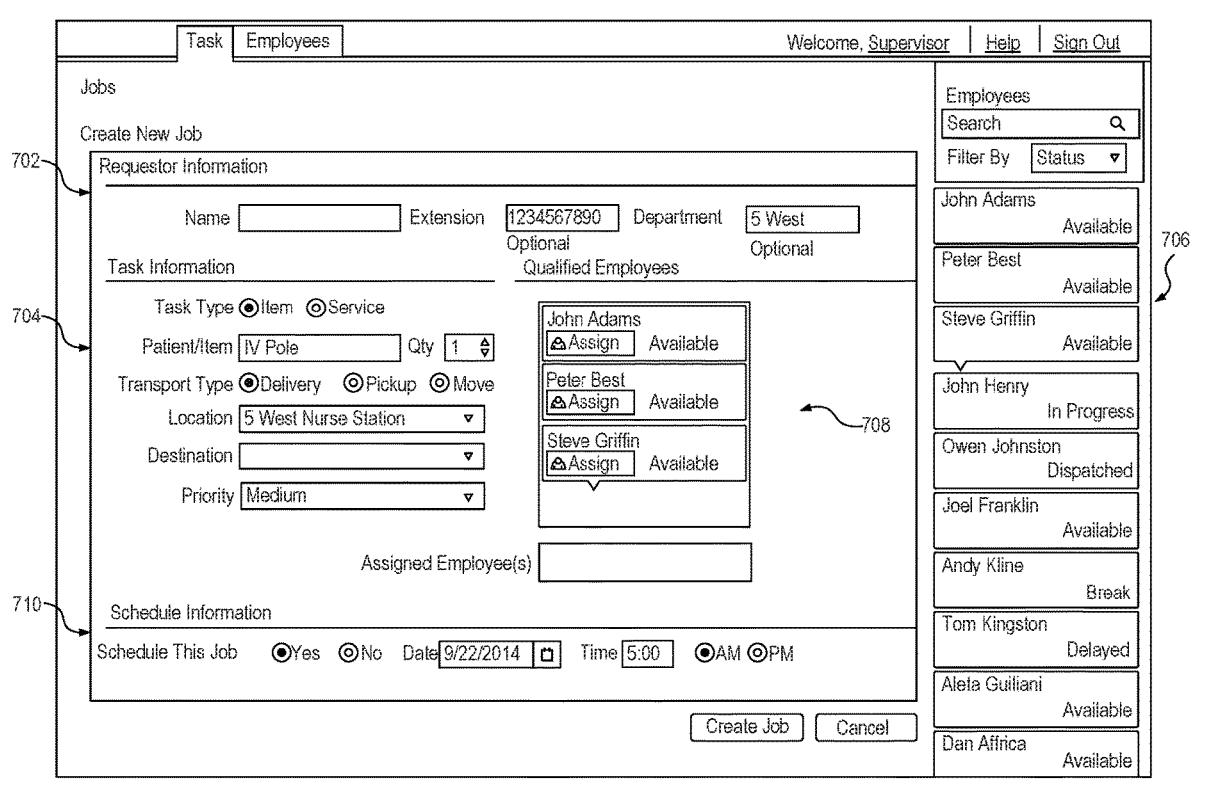

FIG. 7 is an illustration of an example of a user interface 700, consistent with disclosed embodiments. Processor 220, 330 may display user interface 700 in response to a command by user 125 seeking to transport a patient and/or item (e.g., at step 502). After user 125 inputs data pertaining to the request, processor 220, 330, may generate a data packet for the task request, and transmit it through network 150 to server 160, database 180, other computer terminals 140, and/or other user devices 120.

User interface 700 may include a number of different data fields related to a request. The data fields may include requester information 702, task information 704, available employee information 706, qualified employee information 708, and schedule information 710. As further depicted in FIG. 7, requester information 702 may include data fields for a name, an extension, and a department of the requester. Task information 704 may include task type, patient/item, transport type, location, destination, and priority. For example, information 702, 704 may provide data for steps 502 to process a task request. Available employee information 706 may include one or more employees that may be assigned to the task and a status for each of the employees. In some embodiments, available employee information 706 may be auto-populated from one or more of database 180, memory 250, memory 340, and database 470, and may be, for example, provided to step 504. Qualified employee information 708 may include a subset of the employees of available employees 706. In some embodiments, qualified employee information 708 may be determined by network server 160, for example, in step 506. Schedule information 710 may include an input, received from the user, to schedule the job. Preferably, the requested task may be scheduled for the current time, but can also be delayed according to input into schedule information 710.

Figure 8:
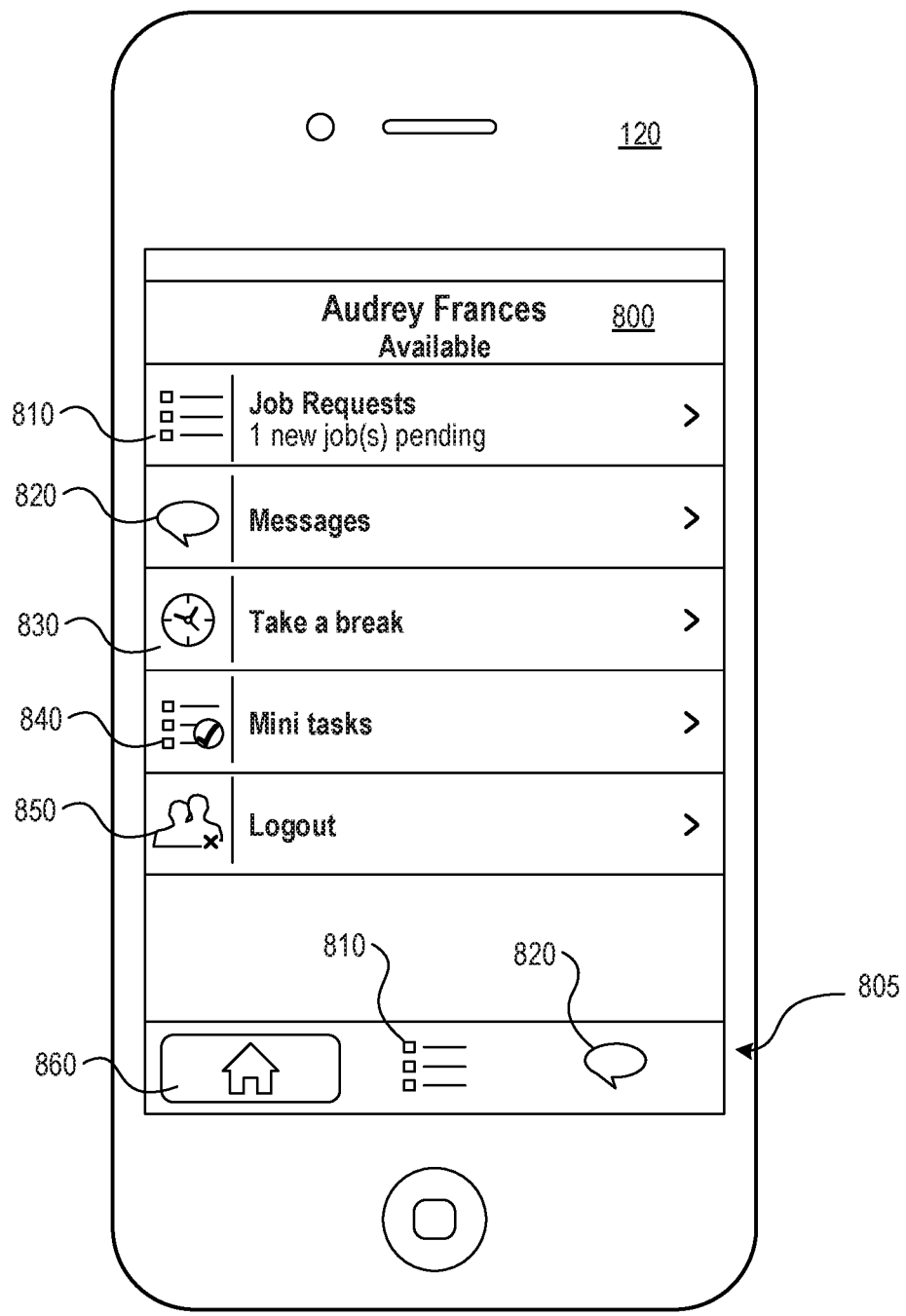
FIG. 8 is an illustration of an example of a mobile device user interface, consistent with embodiments of the present disclosure.

FIG. 8 is an illustration of an example of a mobile device interactive graphical user interface 800, consistent with embodiments of the present disclosure. Interface 800 may be provided, for example, on display 310 of user device 120 to provide user 125 access and/or management of transporting job functions. In some embodiments, interface 800 may provide a home menu with a plurality of icons that provide access to transporting job functions, for example, the home menu may include a job request icon 810, a messages icon 820, a break icon 830, a mini tasks icon 840, and a logout icon 850. Transport tracking user interface 800 may also provide a task bar 805 including a home icon 860, job request icon 810, and messages icon 820. When user 125 selects an icon 810-860, user device 120 may display additional user interfaces to provide access and/or management of transporting job functions. For example, in some embodiments, when user 125 selects break icon 830 user device 120 may display a break user interface (not shown) that allows user 125 to indicate whether user 125 is going on either a lunch break of a scheduled break. Network server 160 may process and update the data pertaining to the specific user 125. In some embodiments, user device 120 may display one or more additional user interfaces associated with a transport request. For example, user device 120 may display a user interface detailing a new or current transport request, and provide one or more user-selectable buttons for accepting or bypassing the transport request (not shown).

Figure 9:
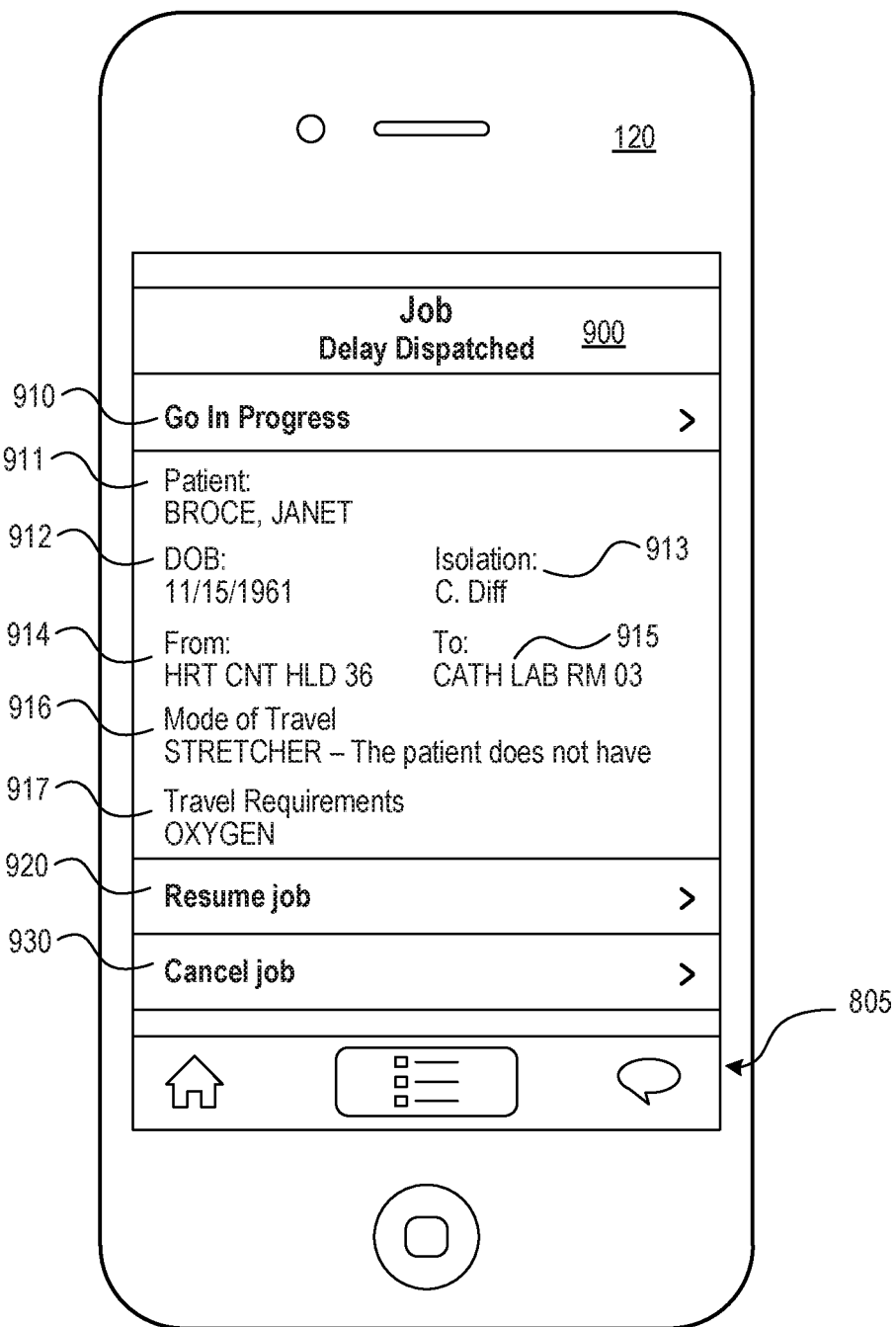
FIG. 9 is an illustration of an example of a job status mobile device user interface, consistent with embodiments of the present disclosure.

FIG. 9 is an illustration of an example of a job status interactive graphical user interface 900, consistent with embodiments of the present disclosure. In some embodiments, job status user interface 900 may provide a job progress button 910, a resume job button 920, and a cancel job button 930 that may allow the user 125 to access data and manage pending jobs. For example, job progress button 910 may be selected to cause generation and display of data fields detailing the current transport job, such as a patient name field 911, a date of birth field 912, an isolation field 913, an original location field 914, a destination field 915, a mode of travel field 916, and a travel requirements field 917. Data fields 911-916 may be dynamically generated based on the patient and/or item to be transported. For example, when a transport job for an item is received, job status user interface 900 may provide data fields that display specific information for the item. Resume job button 920 may be selected to enable user 125 to resume a job that is currently pending, and cancel job button 930 may be selected to enable user 125 to cancel a job that is currently pending. Job status user interface 900 may also provide task bar 805, as discussed with regard to FIG. 8, which may indicate the current user interface displayed.

Figure 10:
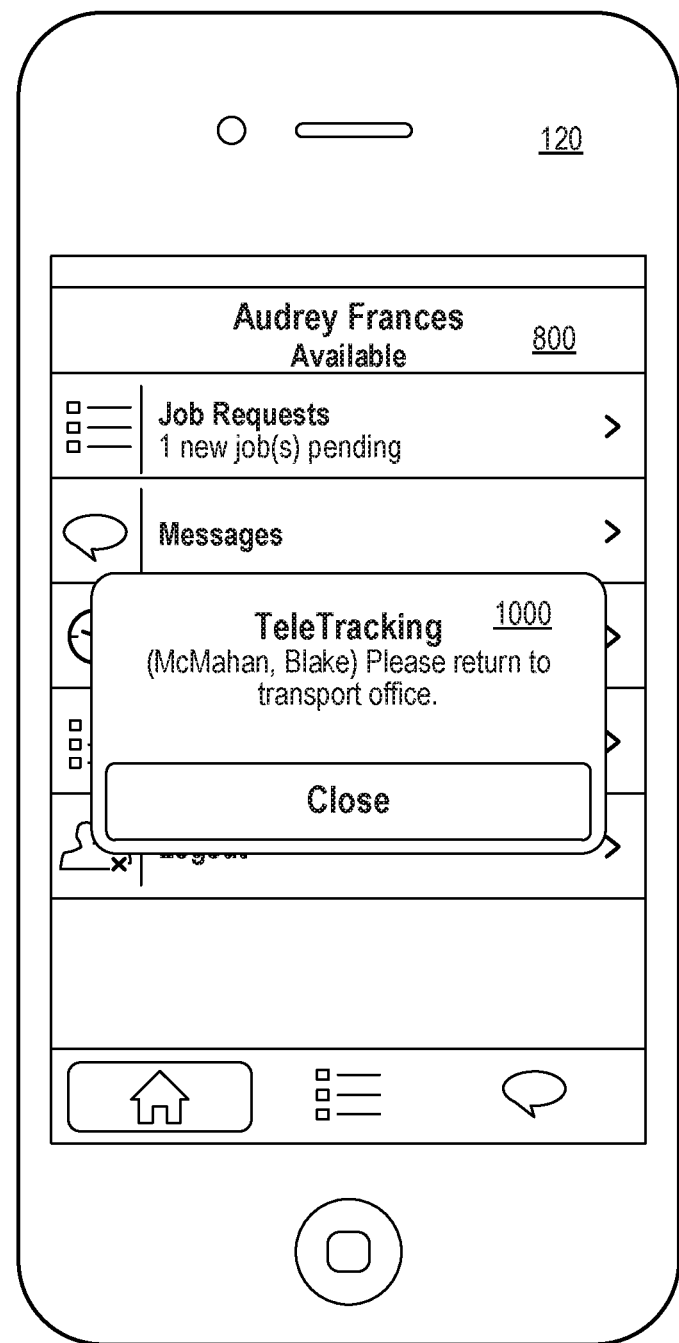
FIG. 10 is an illustration of an example of a push notification mobile device user interface, consistent with embodiments of the present disclosure.

FIG. 10 is an illustration of an example of a push notification interface 1000, consistent with embodiments of the present disclosure. For example, network server 160 may display push notification interface 1000 on one or more user devices 120 to provide an immediate notification to one or more users 125. As illustrated in FIG. 10, push notification interface 1000 may overlay other user interfaces, such as interface 800. Network server 160 may data transmit associated with push notification interface 1000 to be automatically displayed on a plurality of user devices 120 in order locate an employee. Push notification interface 1000 may also be generated based on other statuses related to transport requests, such as indicating a change in a job status or an alert condition detected for one or more jobs.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A system in a healthcare facility comprising:
a server comprising one or more processors and one or more storage devices, the server being in communication with a plurality of mobile devices associated with a plurality of employees comprising transporters;
a computer terminal; and
a location system comprising a plurality of wireless receivers,
wherein the one or more storage devices comprise instructions that, when executed, configure the one or more processors to perform operations comprising:
receiving a transportation request from the computer terminal, the request being associated with a first department of the healthcare facility and requesting the transportation of an object comprising at least one of: a patient and an item, wherein the transportation request identifies a destination location of the object;
receiving, from the location system, location data associated with the plurality of mobile devices, wherein the location data identifies a current location of the plurality of mobile devices;
accessing a look-up table to retrieve attributes associated with the plurality of employees, wherein the attributes comprise a current availability of the plurality of employees;
generating an assignment for a selected employee from the plurality of employees based on the attributes, the location data, and the request; and
generating first GUI instructions to display a first GUI in one of the plurality of mobile devices associated with the selected employee, the first GUI comprising:
a first interactive icon indicating an assignment status, wherein the assignment status indicates an assignment of the transportation request to the selected employee; and
a second interactive icon configured to generate a response message and transmit the response message to the server, wherein the response message is generated in response to the selected employee interacting with the first interactive icon.

2. The system of claim 1, wherein the operations further comprise:
generating second GUI instructions for updating a second GUI displayed in the computer terminal, the second GUI comprising:
a first window displaying a list of the plurality of employees; and
a second window comprising a subset of the plurality of employees that are qualified to fulfill the request.

3. The system of claim 2, wherein the operations further comprise:
monitoring whether the selected employee has interacted with the first GUI;
generating third GUI instructions when determining the selected employee has interacted with the first GUI, the third GUI instructions comprising instructions to update the second GUI to indicate the selected employee interacted with the first GUI; and
transmitting the third GUI instructions to the computer terminal.

4. The system of claim 2, wherein the operations further comprise transmitting the first GUI instructions to the one of the plurality of mobile devices in a first push notification.

5. The system of claim 4, wherein the operations further comprise:
initiating a timer after transmitting the first GUI instructions; and
transmitting third GUI instructions to the one of the plurality of mobile devices in a second push notification, the third GUI instructions comprising instructions to display a reminder message and a button that overlays previous GUIs displayed in the one of the plurality of mobile devices.

6. The system of claim 1, wherein the plurality of mobile devices are associated with transporters responsible for transporting patients or items within the healthcare facility.

7. The system of claim 6, wherein the first interactive icon is configured to display dynamically generated data fields when selected, the dynamically generated data fields comprising patient name, date of birth, original location, mode of travel, and travel requirements.

8. The system of claim 6, wherein the plurality of mobile devices comprise wearable devices.

9. The system of claim 1, wherein:
the one or more processors are coupled in communication with a remote database; and
accessing the look-up table comprises querying the remote database.

10. The system of claim 9, wherein generating the assignment comprises:
retrieving, from the look-up table, job titles, certifications, and skill sets associated with the plurality of employees;
correlating requirements of the request with the job titles, certifications, and skill sets; and
correlating a location associated with the request with the location data.

11. The system of claim 1, wherein the plurality of wireless sensors are configured to track location tags through radio frequency.

12. The system of claim 1, wherein generating the assignment comprises:
receiving equipment location data from the location system;
determining equipment required to fulfill the request; and
adjusting the selected employee based on a distance between the plurality of mobile devices and the equipment required.

13. The system of claim 12, wherein the operations further comprise:
determining whether the equipment required is in possession of one of the plurality of employees; and
adjusting the selected employee based on possession of the equipment required.

14. The system of claim 1, wherein the operations further comprise:
grouping the request with a plurality of requests from other departments of the healthcare facility; and
generating a batched task for the selected employee comprising the grouping.

15. The system of claim 1, wherein the operations further comprise updating a master queue to include the assignment.

16. The system of claim 15, wherein the operations further comprise:
assigning a numerical priority for the assignment; and
storing the request in the master queue in an order determined by the numerical priority.

17. The system of claim 1, wherein the first GUI further comprises:
a task bar with a plurality of icons; and
a third interactive icon configured to display messages.

18. The system of claim 17, wherein the first GUI further comprises a fourth interactive icon configured to logout users.

19. A non-transitory computer-readable medium storing instructions that, when executed by a processor, cause the process to operate an assignments system in a healthcare facility, the operations comprising:
receiving a transportation request from a computer terminal, the request being associated with a first department of the healthcare facility and requesting the transportation of an object comprising at least one of: a patient and an item, wherein the transportation request identifies a destination location of the object;
receiving, from a location system, location data associated with a plurality of mobile devices, the plurality of mobile devices being associated to a plurality of employees comprising transporters, the location system comprising a plurality of wireless receivers, wherein the location data identifies a current location of the plurality of mobile devices;
accessing a look-up table to retrieve attributes associated with the plurality of employees, wherein the attributes comprise a current availability of the plurality of employees;
generating an assignment for a selected employee from the plurality of employees based on the attributes, the location data, and the request; and
generating first GUI instructions to display a first GUI in one of the plurality of mobile devices associated with the selected employee, the first GUI comprising:
a first interactive icon indicating an assignment status, wherein the assignment status indicates an assignment of the transportation request to the selected employee; and
a second interactive icon configured to generate a response message and transmit the response message to the server, wherein the response message is generated in response to the selected employee interacting with the first interactive icon.

20. A computer-implemented method for operating a healthcare facility assignments system, the method comprising:
receiving a transportation request from a computer terminal, the request being associated with a first department of the healthcare facility and requesting the transportation of an object comprising at least one of: a patient and an item, wherein the transportation request identifies a destination location of the object;
receiving, from a location system, location data associated with a plurality of mobile devices, the plurality of mobile devices being associated to a plurality of employees comprising transporters, the location system comprising a plurality of wireless receivers, wherein the location data identifies a current location of the plurality of mobile devices;
accessing a look-up table to retrieve attributes associated with the plurality of employees, wherein the attributes comprise a current availability of the plurality of employees;
generating an assignment for a selected employee from the plurality of employees based on the attributes, the location data, and the request; and
generating first GUI instructions to display a first GUI in one of the plurality of mobile devices associated with the selected employee, the first GUI comprising:
a first interactive icon indicating an assignment status, wherein the assignment status indicates an assignment of the transportation request to the selected employee; and
a second interactive icon configured to generate a response message and transmit the response message to the server, wherein the response message is generated in response to the selected employee interacting with the first interactive icon.

\* \* \* \* \*